United States Patent
Choi

(10) Patent No.: US 12,217,445 B2
(45) Date of Patent: Feb. 4, 2025

(54) PROBABILITY MAP-BASED ULTRASOUND SCANNING

(71) Applicant: Verathon Inc., Bothell, WA (US)

(72) Inventor: Joon Hwan Choi, Bothell, WA (US)

(73) Assignee: Verathon Inc., Bothell, WA (US)

(*) Notice: Subject to any disclaimer, the term of this patent is extended or adjusted under 35 U.S.C. 154(b) by 612 days.

(21) Appl. No.: 15/977,091

(22) Filed: May 11, 2018

(65) Prior Publication Data
US 2018/0330518 A1 Nov. 15, 2018

Related U.S. Application Data

(60) Provisional application No. 62/504,709, filed on May 11, 2017.

(51) Int. Cl.
*G06T 7/62* (2017.01)
*A61B 5/00* (2006.01)
(Continued)

(52) U.S. Cl.
CPC .............. *G06T 7/62* (2017.01); *A61B 5/7267* (2013.01); *A61B 8/085* (2013.01); *A61B 8/0866* (2013.01); *A61B 8/0883* (2013.01); *A61B 8/0891* (2013.01); *A61B 8/14* (2013.01); *A61B 8/42* (2013.01); *A61B 8/463* (2013.01); *A61B 8/5223* (2013.01); *A61B 8/5292* (2013.01);
(Continued)

(58) Field of Classification Search
None
See application file for complete search history.

(56) References Cited

U.S. PATENT DOCUMENTS

| 5,081,933 A | * | 1/1992 | Lapp | ..................... B61D 13/00 105/3 |
| 5,081,993 A | | 1/1992 | Kitney et al. | |

(Continued)

FOREIGN PATENT DOCUMENTS

| JP | H06-233761 A | 8/1994 |
| JP | 2015-154918 A | 8/2015 |

(Continued)

OTHER PUBLICATIONS

Verathon (Feb. 23, 2016). Bladderscan BVM 9500: Operations & Maintenance Manual. Retrieved Mar. 21, 2021, from https://www.verathon.com/wp-content/uploads/product_docs/0900-1596-xx-60.pdf (Year: 2016).*

(Continued)

*Primary Examiner* — Angela M Hoffa
*Assistant Examiner* — Helene Bor
(74) *Attorney, Agent, or Firm* — Snyder, Clark, Lesch & Chung, LLP

(57) ABSTRACT

A system may include a probe configured to transmit ultrasound signals to a target of interest, and receive echo information associated with the transmitted ultrasound signals. The system may also include at least one processing device configured to process the received echo information using a machine learning algorithm to generate probability information associated with the target of interest. The at least one processing device may further classify the probability information and output image information corresponding to the target of interest based on the classified probability information.

23 Claims, 11 Drawing Sheets

(51) Int. Cl.

| | | |
|---|---|---|
| A61B 8/00 | (2006.01) | |
| A61B 8/08 | (2006.01) | |
| A61B 8/14 | (2006.01) | |
| G06N 3/045 | (2023.01) | |
| G06N 3/08 | (2023.01) | |
| G06N 7/01 | (2023.01) | |
| G06T 7/00 | (2017.01) | |
| G16H 30/20 | (2018.01) | |
| G16H 30/40 | (2018.01) | |
| G16H 50/20 | (2018.01) | |

(52) U.S. Cl.

CPC ............ *A61B 8/565* (2013.01); *G06N 3/045* (2023.01); *G06N 3/08* (2013.01); *G06N 7/01* (2023.01); *G06T 7/0014* (2013.01); *G16H 30/20* (2018.01); *G16H 30/40* (2018.01); *G16H 50/20* (2018.01); *A61B 5/4325* (2013.01); *A61B 5/4381* (2013.01); *G06T 2207/10132* (2013.01); *G06T 2207/20081* (2013.01); *G06T 2207/20084* (2013.01); *G06T 2207/30084* (2013.01)

(56) References Cited

U.S. PATENT DOCUMENTS

| | | | |
|---|---|---|---|
| 5,734,739 A * | 3/1998 | Sheehan | G06T 7/12 600/407 |
| 5,871,019 A | 2/1999 | Belohlavek | |
| 5,984,870 A * | 11/1999 | Giger | G06T 7/0012 600/443 |
| 6,238,342 B1 * | 5/2001 | Feleppa | A61B 17/3403 600/437 |
| 6,585,647 B1 | 7/2003 | Winder | |
| 6,932,770 B2 | 8/2005 | Hastings et al. | |
| 7,242,793 B2 | 7/2007 | Trobaugh et al. | |
| 7,555,151 B2 | 6/2009 | Comaniciu et al. | |
| 7,627,386 B2 | 12/2009 | Mo et al. | |
| 7,666,138 B2 | 2/2010 | Ogawa | |
| 7,720,269 B2 | 5/2010 | Okada et al. | |
| 7,744,534 B2 | 6/2010 | Chalana et al. | |
| 7,831,088 B2 | 11/2010 | Li | |
| 8,047,990 B2 | 11/2011 | Burdette et al. | |
| 8,078,255 B2 | 12/2011 | Bhandarkar et al. | |
| 8,157,736 B2 | 4/2012 | Slabaugh et al. | |
| 8,167,803 B2 | 5/2012 | McMorrow et al. | |
| 8,300,909 B2 | 10/2012 | Chouno | |
| 8,308,644 B2 | 11/2012 | McMorrow et al. | |
| 8,343,053 B2 | 1/2013 | Feng et al. | |
| 8,357,094 B2 | 1/2013 | Mo et al. | |
| 8,396,268 B2 | 3/2013 | Zabair et al. | |
| 8,435,181 B2 | 5/2013 | Yang et al. | |
| 8,467,856 B2 | 6/2013 | Renisch et al. | |
| 8,520,976 B2 | 8/2013 | Kaiser et al. | |
| 8,532,360 B2 | 9/2013 | Suri | |
| 8,634,616 B2 | 1/2014 | Den Harder et al. | |
| 8,639,001 B2 | 1/2014 | Nakano et al. | |
| 8,840,555 B2 | 9/2014 | Miller et al. | |
| 8,905,932 B2 | 12/2014 | Lovoi et al. | |
| 9,364,196 B2 | 6/2016 | El-Aklouk et al. | |
| 10,430,688 B2 | 10/2019 | Rao et al. | |
| 2006/0079778 A1 | 4/2006 | Mo et al. | |
| 2009/0030326 A1 | 1/2009 | Kim et al. | |
| 2009/0082691 A1 * | 3/2009 | Denison | A61B 5/374 600/544 |
| 2009/0093717 A1 * | 4/2009 | Carneiro | G06F 19/00 600/443 |
| 2009/0264757 A1 | 10/2009 | Yang et al. | |
| 2010/0067754 A1 * | 3/2010 | Collins | G06T 7/0012 382/128 |
| 2010/0160785 A1 | 6/2010 | Poland et al. | |
| 2010/0166276 A1 * | 7/2010 | Dube | G06T 5/002 382/131 |
| 2011/0137172 A1 | 6/2011 | Kim et al. | |
| 2011/0257527 A1 * | 10/2011 | Suri | G06T 7/13 600/440 |
| 2012/0053467 A1 | 3/2012 | Betts | |
| 2014/0024937 A1 | 1/2014 | Kim et al. | |
| 2014/0052001 A1 | 2/2014 | Ionasec et al. | |
| 2014/0350404 A1 * | 11/2014 | Rajguru | A61B 8/466 600/443 |
| 2015/0070385 A1 * | 3/2015 | Ishizu | A61B 8/5261 345/632 |
| 2015/0230773 A1 * | 8/2015 | Cho | A61B 8/0825 382/128 |
| 2016/0113630 A1 | 4/2016 | Chang et al. | |
| 2016/0120502 A1 * | 5/2016 | Sadeghi-Naini | A61B 8/08 600/443 |
| 2016/0270757 A1 | 9/2016 | Toma et al. | |
| 2016/0350620 A1 | 12/2016 | Rao et al. | |
| 2017/0270664 A1 * | 9/2017 | Hoogi | A61B 6/5217 |
| 2018/0140281 A1 | 5/2018 | Imai | |
| 2018/0140282 A1 | 5/2018 | Toyomura et al. | |
| 2019/0392243 A1 * | 12/2019 | Dufort | G06T 7/0012 |
| 2020/0074271 A1 * | 3/2020 | Liang | G06N 3/084 |

FOREIGN PATENT DOCUMENTS

| | | | | |
|---|---|---|---|---|
| JP | 2016-221264 A | 12/2016 | | |
| JP | 6200249 B2 | 9/2017 | | |
| WO | WO-0182787 A2 * | 11/2001 | ............. | A61B 6/481 |
| WO | 2014/076931 A | 1/2017 | | |
| WO | 2017/033502 A | 2/2018 | | |
| WO | 2016/194161 A | 3/2018 | | |

OTHER PUBLICATIONS

Volcano. (2005). s5i Imaging System Intravascular Ultrasound Service Manual. Volcano Corporation (Year: 2005).*

Farhad Imani et al., Ultrasound-Based Characterization of Prostate Cancer Using Joint Independent Component Analysis, IEEE Transactions on Biomedical Engineering, vol. 62, No. 7: 1796-1804, Jul. 7, 2015.

International Search Report and Written Opinion issued in corresponding International Application No. PCT/US2018/032247, mailed on Sep. 20, 2018, 15 pages.

P. Looney et al., "Automatic 3D ultrasound segmentation of the first trimester placenta using deep learning," 2017 IEEE 14th International Symposium on Biomedical Imaging (ISBI 2017), Melbourne, VIC, Australia, 2017, pp. 279-282.

Mahsa Shakeri, Stavros Tsogkas, Enzo Ferrante, Sarah Lippe, Samuel Kadoury, et al. Sub-cortical brain structure segmentation using F-CNN's. ISBI 2016: International Symposium on Biomedical Imaging, 2016, 6 pages, Prague, Czech Republic.

Mcube Technology Co., BioCon-700 Operator Manual (Revision Date: Nov. 21, 2016), 174 pages.

Biological Image Reconstruction and Analysis, Nov. 17, 2016, Berlin, Ignacio Arganda-Carreras, presentation materials, 78 pages.

K. Kamnitsas et al. "Efficient multi-scale 3D CNN with fully connected CRF for accurate brain lesion segmentation." Medical Image Analysis 36 (2017), pp. 61-78.

Raon People Machine Learning Academy: Semantic Segmentation: 1. Basic theory of Image Segmentation [1]. https://blog.naver.com/laonple/220873446440, Nov. 29, 2016 (machine translation), 7 pages.

Raon People Machine Learning Academy: Semantic Segmentation 1. ImageSegmentation. Basic Theory [2]. https://blog.naver.com/laonple/220874313327. Nov. 30, 2016 (machine translation), 8 pages.

Raon People Machine Learning Academy: Semantic Segmentation 3. FCN [1] https://m.blog.naver.com/laonple/220958109081. Mar. 14, 2017 (machine translation), 7 pages.

* cited by examiner

PROBABILITY MAP-BASED ULTRASOUND SCANNING

RELATED APPLICATION

This application claims priority under 35 U.S.C. § 119 based on U.S. Provisional Application No. 62/504,709 filed May 11, 2017, the contents of which are hereby incorporated herein by reference in their entirety.

BACKGROUND INFORMATION

Ultrasound scanners are typically used to identify a target organ or other structures in the body and/or determine features associated with the target organ/structure, such as the size of the organ/structure or the volume of fluid in the organ. For example, ultrasound scanners are used to identify a patient's bladder and estimate the volume of fluid in the bladder. In typical scenarios, the ultrasound scanner is placed on the patient and triggered to generate ultrasound signals which comprise sound waves output at a specific frequency. The echoes from the ultrasound signals may be received by the scanner and analyzed to determine the volume of fluid in the bladder. For example, the received echoes may be used to generate corresponding images that can be analyzed to detect boundaries of the target organ, such as the bladder wall. The volume of the bladder may then be estimated based on the detected boundary information. However, typical ultrasound scanners often suffer from inaccuracies caused by a number of factors, such as the variability of the size and/or shape of the target organ of interest from patient to patient, obstructions in the body that make it difficult to accurately detect boundaries of the target organ/structure, etc.

DETAILED DESCRIPTION OF PREFERRED EMBODIMENTS

The following detailed description refers to the accompanying drawings. The same reference numbers in different drawings may identify the same or similar elements. Also, the following detailed description does not limit the invention.

Implementations described herein relate to using machine learning, including using neural networks and deep learning, to identify an organ or structure of interest in a patient based on information obtain via an ultrasound scanner. For example, the scanner may be used to transmit a number of ultrasound signals toward the target organ and echo information associated with transmitted signals may be processed using machine learning techniques/algorithms. The machine learning processing may be used to identify the target of interest and generate probability information associated with each portion or pixel of an image generated based on the received ultrasound echo data.

For example, in one implementation, ultrasound echo data, such as B-mode echo data associated with ultrasound signals transmitted on a number of different scan planes directed to the target organ, may be used to generate a probability map for each B-mode image. In one implementation, each pixel in the B-mode image may be mapped to a probability indicating whether that particular pixel is within or part of the target organ/structure. The result of the pixel-by-pixel analysis is used to generate a target probability map. A binarization process and post-processing may then be performed to remove noise and provide a more accurate representation of the organ, as compared to conventional scanners that attempt to determine boundary walls for the target organ and estimate the size based on the boundary information. In some implementations, the output from the post-processing is displayed to medical personnel and may aid in easily locating the organ while performing the ultrasound scan. Additional post-processing may also be performed to estimate a volume for the target organ, such as the volume of fluid in a patient's bladder.

Figure 1A:
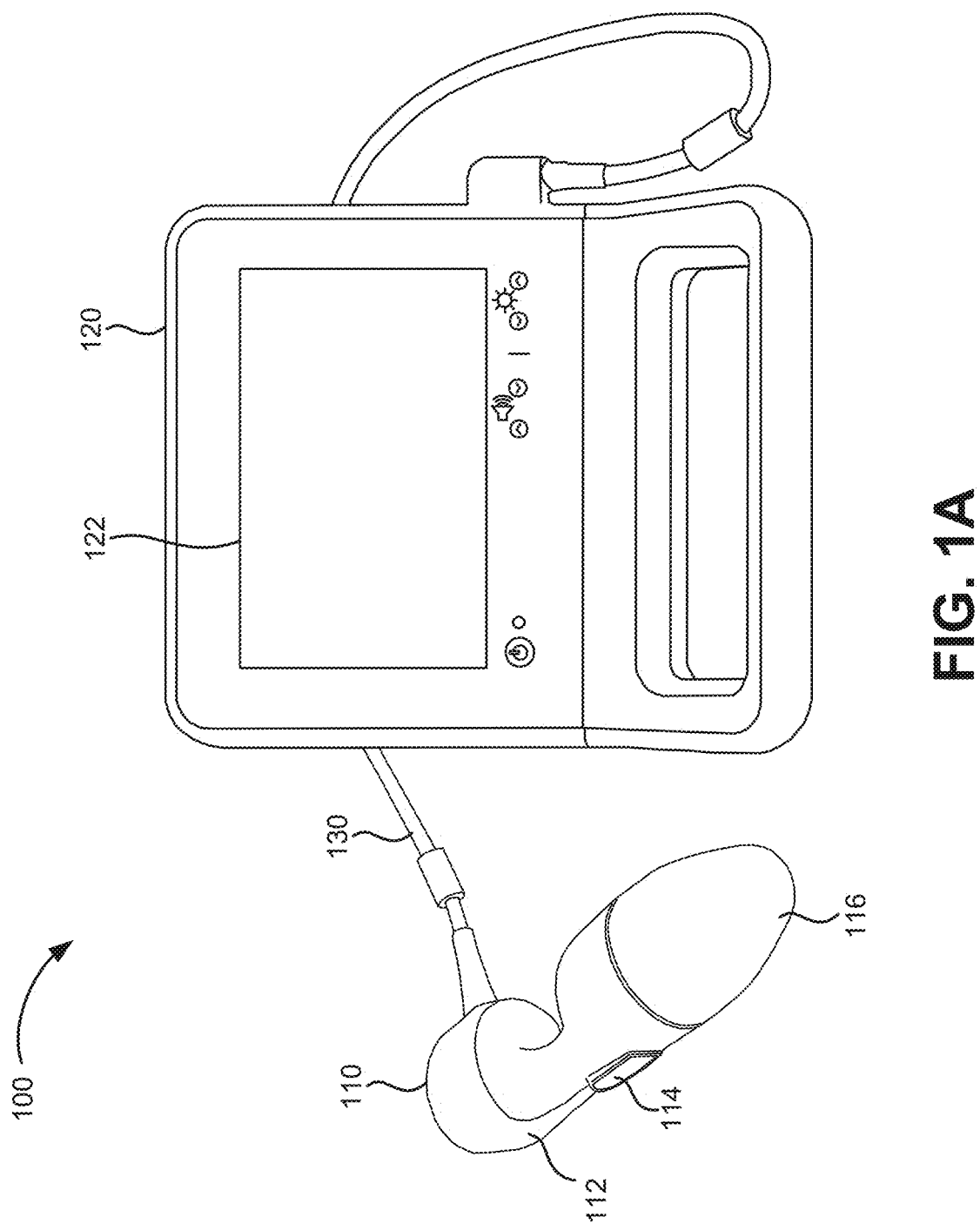
FIG. 1A illustrates an exemplary configuration of a scanning system consistent with an exemplary implementation.

FIG. 1A is a diagram illustrating a scanning system 100 consistent with an exemplary embodiment. Referring to FIG. 1, scanning system 100 includes probe 110, base unit 120 and cable 130.

Probe 110 includes handle portion 112 (also referred to as handle 112), trigger 114 and nose portion 116 (also referred to as dome or dome portion 116). Medical personnel may hold probe 110 via handle 112 and press trigger 114 to activate one or more ultrasound transceivers and transducers located in nose portion 116 to transmit ultrasound signals toward the target organ of interest. For example, FIG. 1B illustrates probe 110 located on the pelvic area of patient 150 and over a target organ of interest, which in this example is the patient's bladder 152.

Handle 112 allows a user to move probe 110 relative to patient 150. As discussed above, trigger 114 initiates an ultrasound scan of a selected anatomical portion while dome 116 is in contact with a surface portion of patient 150 when the selected anatomical portion is scanned. Dome 116 is typically formed of a material that provides an appropriate acoustical impedance match to the anatomical portion and/or permits ultrasound energy to be properly focused as it is projected into the anatomical portion. For example, an acoustic gel or gel pads, illustrated at area 154 in FIG. 1B, may be applied to patient 150's skin over the region of interest (ROI) to provide an acoustical impedance match when dome 116 is placed against patient 150's skin.

Figure 1B:
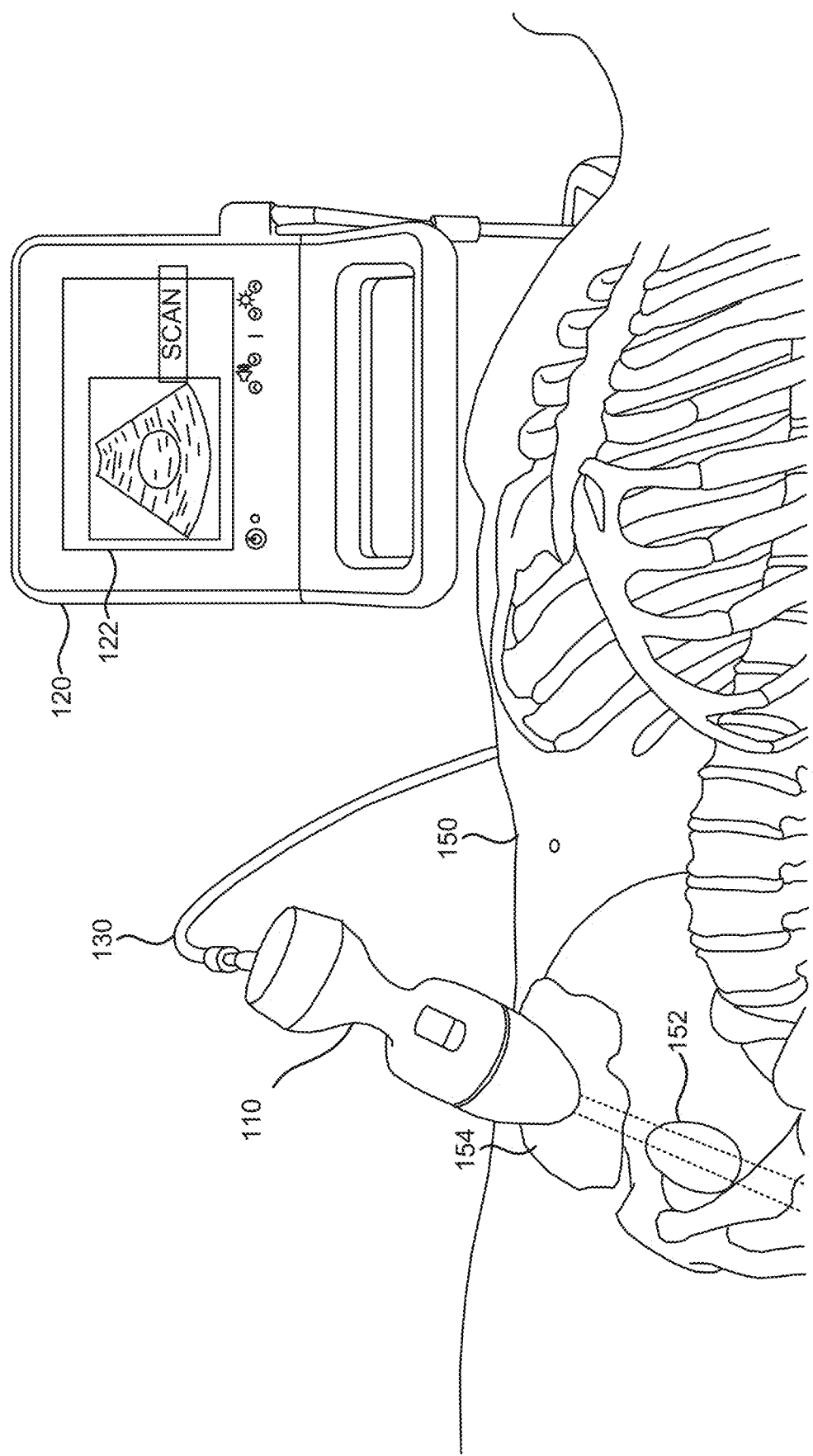
FIG. 1B illustrates operation of the scanning system of FIG. 1A with respect to detecting an organ in a patient.

Dome 116 includes one or more ultrasound transceiver elements and one or more transducer elements (not shown in FIG. 1A or 1B). The transceiver elements transmit ultrasound energy outwardly from the dome 116, and receive acoustic reflections or echoes generated by internal structures/tissue within the anatomical portion. The one or more ultrasound transducer elements may include a one-dimensional, or a two-dimensional array of piezoelectric elements that may be moved within dome 116 by a motor to provide different scan directions with respect to the transmissions of ultrasound signals by the transceiver elements. Alternatively, the transducer elements may be stationary with respect to probe 110 so that the selected anatomical region may be scanned by selectively energizing the elements in the array.

In some implementations, probe 110 may include a directional indicator panel (not shown in FIG. 1A) that includes a number of arrows that may be illuminated for initial targeting and guiding a user to access the targeting of an organ or structure within the ROI. For example, in some implementations, if the organ or structure is centered from placement of probe 110 placed against the dermal surface at a first location of patient 150, the directional arrows may be not illuminated. However, if the organ is off-center, an arrow or set of arrows may be illuminated to direct the user to reposition probe 110 at a second or subsequent dermal location of patient 150. In other implementations, the directional indicators may be presented on display 122 of base unit 120.

The one or more transceivers located in probe 110 may include an inertial reference unit that includes an accelerometer and/or gyroscope positioned preferably within or adjacent to dome 116. The accelerometer may be operable to sense an acceleration of the transceiver, preferably relative to a coordinate system, while the gyroscope may be operable to sense an angular velocity of the transceiver relative to the same or another coordinate system. Accordingly, the gyroscope may be of a conventional configuration that employs dynamic elements, or it may be an optoelectronic device, such as an optical ring gyroscope. In one embodiment, the accelerometer and the gyroscope may include a commonly packaged and/or solid-state device. In other embodiments, the accelerometer and/or the gyroscope may include commonly packaged micro-electromechanical system (MEMS) devices. In each case, the accelerometer and gyroscope cooperatively permit the determination of positional and/or angular changes relative to a known position that is proximate to an anatomical region of interest in the patient.

Probe 110 may communicate with base unit 120 via a wired connection, such as via cable 130. In other implementations, probe 110 may communicate with base unit 120 via a wireless connection (e.g., Bluetooth, WiFi, etc.). In each case, base unit 120 includes display 122 to allow a user to view processed results from an ultrasound scan, and/or to allow operational interaction with respect to the user during operation of probe 110. For example, display 122 may include an output display/screen, such as a liquid crystal display (LCD), light emitted diode (LED) based display, or other type of display that provides text and/or image data to a user. For example, display 122 may provide instructions for positioning probe 110 relative to the selected anatomical portion of patient 150. Display 122 may also display two-dimensional or three-dimensional images of the selected anatomical region.

In some implementations, display 122 may include a graphical user interface (GUI) that allows the user to select various features associated with an ultrasound scan. For example, display 122 may allow a user to select whether patient 150 is male, female or a child. This allows system 100 to automatically adapt the transmission, reception and processing of ultrasound signals to the anatomy of a selected patient, such as adapt system 100 to accommodate various anatomical details of male and female patients. For example, when a male patient is selected via the GUI on display 122, system 100 may be configured to locate a single cavity, such as a urinary bladder in the male patient. In contrast, when a female patient is selected via the GUI, system 100 may be configured to image an anatomical portion having multiple cavities, such as a bodily region that includes a bladder and a uterus. Similarly, when a child patient is selected, system 100 may be configured to adjust the transmission based on the smaller size of the child patient. In alternative implementations, system 100 may include a cavity selector configured to select a single cavity scanning mode, or a multiple cavity-scanning mode that may be used with male and/or female patients. The cavity selector may thus permit a single cavity region to be imaged, or a multiple cavity region, such as a region that includes an aorta and a heart to be imaged. In addition, the selection of the type of patient (e.g., male, female, child) may be used when analyzing the images to aid in providing an accurate representation of the target organ, as described in detail below.

To scan a selected anatomical portion of a patient, dome 116 may be positioned against a surface portion of patient 150 as illustrated in FIG. 1B that is proximate to the anatomical portion to be scanned. The user actuates the transceiver by depressing trigger 114. In response, the transducer elements optionally position the transceiver, which transmits ultrasound signals into the body, and receives corresponding return echo signals that may be at least partially processed by the transceiver to generate an ultrasound image of the selected anatomical portion. In a particular embodiment, system 100 transmits ultrasound signals in a range that extends from approximately about two megahertz (MHz) to approximately 10 or more MHz (e.g., 18 MHz).

In one embodiment, probe 110 may be coupled to a base unit 120 that is configured to generate ultrasound energy at a predetermined frequency and/or pulse repetition rate and to transfer the ultrasound energy to the transceiver. Base unit 120 also includes one or more processors or processing logic configured to process reflected ultrasound energy that is received by the transceiver to produce an image of the scanned anatomical region.

In still another particular embodiment, probe 110 may be a self-contained device that includes a microprocessor positioned within the probe 110 and software associated with the microprocessor to operably control the transceiver, and to process the reflected ultrasound energy to generate the ultrasound image. Accordingly, a display on probe 110 may be used to display the generated image and/or to view other information associated with the operation of the transceiver. For example, the information may include alphanumeric data that indicates a preferred position of the transceiver prior to performing a series of scans. In other implementations, the transceiver may be coupled to a general-purpose computer, such as a laptop or a desktop computer that includes software that at least partially controls the operation of the transceiver, and also includes software to process information transferred from the transceiver so that an image of the scanned anatomical region may be generated.

Figure 2:
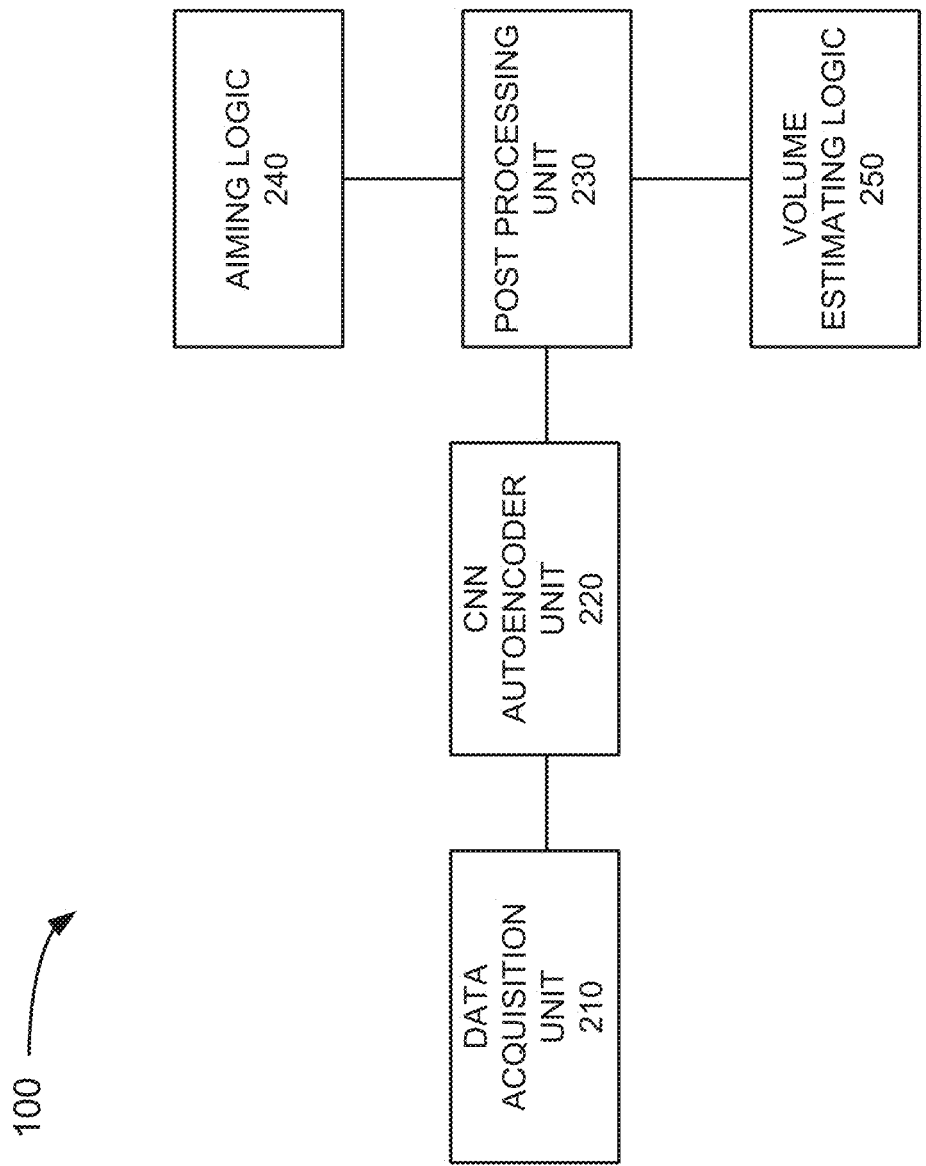
FIG. 2 illustrates an exemplary configuration of logic elements included in the scanning system of FIG. 1A.

FIG. 2 is a block diagram of functional logic components implemented in system 100 in accordance with an exemplary implementation. Referring to FIG. 2, system 100 includes data acquisition unit 210, convolutional neural network (CNN) autencoder unit 220, post processing unit 230, aiming logic 240 and volume estimating logic 250. In an exemplary implementation, probe 110 may include data acquisition unit 210 and the other functional units (e.g., CNN autoencoder unit 220, post processing unit 230, aiming logic 240 and volume estimating logic 250) may be implemented in base unit 120. In other implementations, the particular units and/or logic may be implemented by other devices, such as via computing devices or servers located externally with respect to both probe 110 and base unit 120 (e.g., accessible via a wireless connection to the Internet or to a local area network within a hospital, etc.). For example, probe 110 may transmit echo data and/or image data to a processing system via, for example, a wireless connection (e.g., WiFi or some other wireless protocol/technology) that is located remotely from probe 110 and base unit 120.

As described above, probe 110 may include a transceiver that produces ultrasound signals, receives echoes from the transmitted signals and generates B-mode image data based on the received echoes (e.g., the magnitude or intensity of the received echoes). In an exemplary implementation, data acquisition unit 210 obtains data associated with multiple scan planes corresponding to the region of interest in patient 150. For example, probe 110 may receive echo data that is processed by data acquisition unit 210 to generate two-dimensional (2D) B-mode image data to determine bladder size and/or volume. In other implementations, probe 110 may receive echo data that is processed to generate three-dimensional (3D) image data that can be used to determine bladder size and/or volume.

Figure 3:
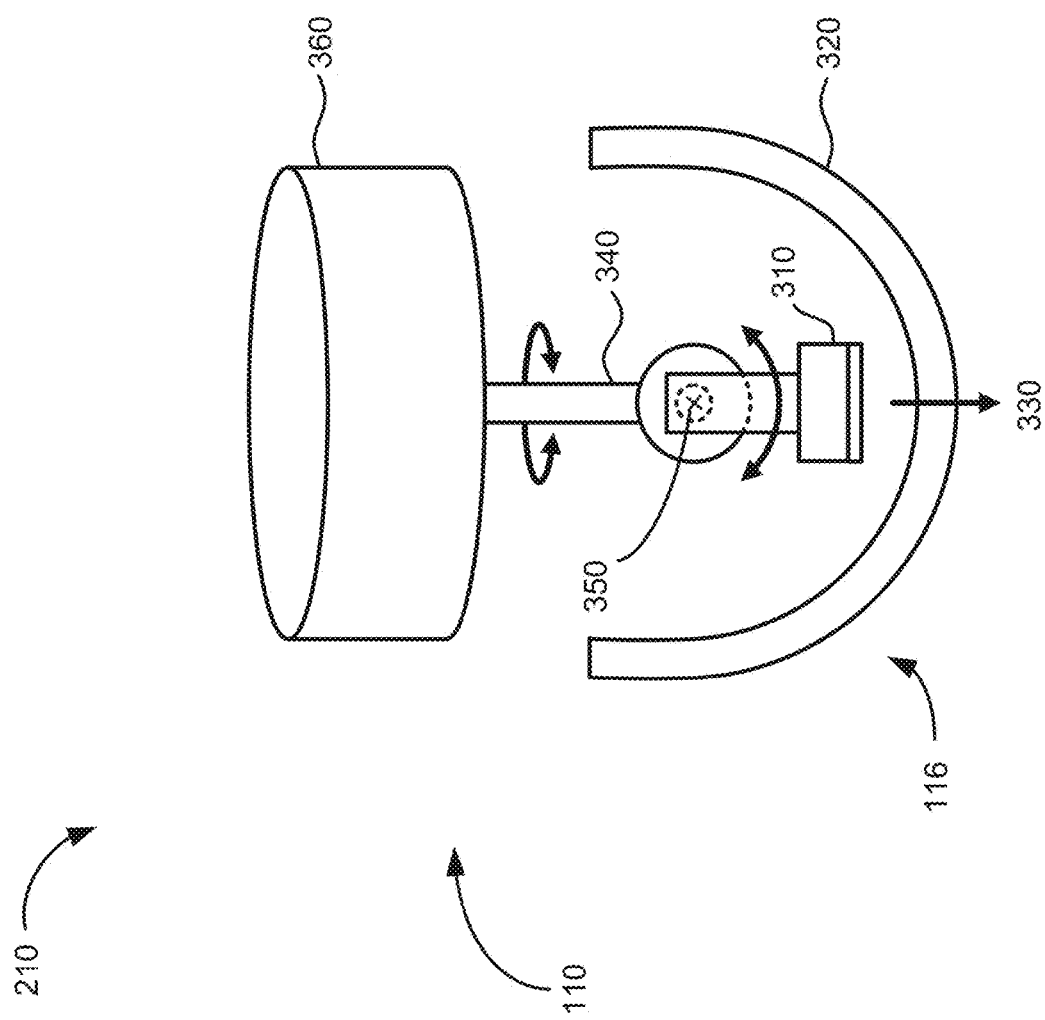
FIG. 3 illustrates a portion of the data acquisition unit of FIG. 2 in an exemplary implementation.

For example, FIG. 3 illustrates an exemplary data acquisition unit 210 used to obtain 3D image data. Referring to FIG. 3, data acquisition unit 210 includes transducer 310, outer surface 320 of dome portion 116 and base 360. The elements illustrated in FIG. 3 may be included within dome portion 116 of probe 110.

Transducer 310 may transmit ultrasound signals from probe 110, indicated by 330 in FIG. 3. Transducer 310 may be mounted to allow transducer 310 to rotate about two perpendicular axes. For example, transducer 310 may rotate around a first axis 340 with respect to base 360 and rotate around a second axis 350 with respect to base 360. The first axis 340 is referred to herein as the theta axis and the second axis 350 is referred to herein as the phi axis. In an exemplary implementation, the range of theta and phi motion may be less than 180 degrees. In one implementation, the scanning may be interlaced with respect to the theta motion and phi motion. For example, movement of transducer 310 may occur in the theta direction followed by movement in the phi direction. This enables data acquisition unit 210 to obtain smooth continuous volume scanning as well as improving the rate at which the scan data is obtained.

In an exemplary implementation, data acquisition unit 210 may resize the B-mode images prior to forwarding the image to CNN autoencoder unit 220. For example, data acquisition unit 210 may include logic to reduce the size of the B-mode images through a reduction or decimation process. The reduced size B-mode images may then be input to CNN autoencoder unit 220, which will generate an output probability mapping, as described in more detail below. In alternative implementations, CNN autoencoder unit 220 may reduce or decimate the input B-mode image itself at the input layer. In either case, reducing the size/amount of B-mode image data may reduce the processing time and processing capability needed by CNN autoencoder unit 220 to process the B-mode image data. In other implementations, no resizing may be performed by data acquisition unit 210 prior to inputting the B-mode image data to CNN autoencoder unit 220. In still other implementations, image enhancement operations, such as brightness normalization, contrast enhancement, scan conversion may be performed by data acquisition unit 210 and/or CNN autoencoder unit 220 to improve accuracy with respect to generating output data.

Referring back to FIG. 2, CNN autoencoder unit 220 may include logic for processing data received via data acquisition unit 210. In an exemplary implementation, CNN autencoder unit 220 may perform deep neural network (DNN) processing that includes a number of convolutional layer processings and a number of kernels or filters for each layer, as described in more detail below. The term "CNN autoencoder unit" or "autoencoder unit" as used herein should be broadly construed to include a neural network and/or machine learning system/unit in which both the input and output have spatial information, in contrast to classifiers that outputs global labels without spatial information.

For example, CNN autoencoder unit 220 includes logic that maps received image input to output with a least possible amount of distortion. CNN processing may be similar to other types of neural network processing, but CNN processing uses the explicit assumption that the inputs are images, which allows the CNN processing to more easily encode various properties/limitations into the processing, thereby reducing the amount of parameters that must be processed or factored by CNN autoencoder unit 220. In an exemplary implementation, CNN autoencoder unit 220 performs convolutional processing to generate features maps associated with the input image. The feature maps may then be sampled a number of times to generate an output. In an exemplary implementation, the kernel size of the CNN used by CNN autoencoder unit 220 may have a size of 17×17 or smaller to provide adequate speed for generating an output. In addition, the 17×17 kernel size allows CNN autoencoder unit 220 to capture adequate information around a point of interest within B-mode image data. In addition, in accordance with an exemplary implementation, the number of convolutional layers may be eight or less with five or less kernels for each layer. However, it should be understood that smaller kernel sizes (e.g., 3×3, 7×7, 9×9, etc.) or larger kernel sizes (e.g., greater than 17×17), additional kernels per layer (e.g., greater than five) and additional convolutional layers (e.g., more than ten and up to hundreds) may be utilized in other implementations.

In typical applications involving CNN processing, the data dimension is reduced by adding a narrow bottleneck layer within the processing such that only the data of interest can pass through the narrow layer. This data dimension reduction is typically accomplished by adding "pooling" layers or using a large "stride" to reduce the size of the image processed by the neural network. However, in some implementations described herein with respect to bladder detection, where spatial precision of a detected bladder wall location is important for accurate volume calculation, pooling and/or large stride is minimally used or combined with other spatial resolution-preserving techniques, such as skip connection or dilated convolution.

While exemplary system 100 depicts using CNN autoencoder unit 220 to process the B-mode input data, in other implementations, system 100 may include other types of autoencoder units or machine learning units. For example, CNN autoencoder unit 220 may include a neural network structure in which the output layer has the same number of nodes as the input layer. In other implementations, other types of machine learning modules or units may be used in which the size of the input layers does not equal the size of the output layers. For example, a machine learning module may generate a probability mapping output that is two times larger or smaller (in terms of the number of layers) than the input image. In other implementations, a machine learning unit included in system 100 may use various machine learning techniques and algorithms, such as decision trees, support vector machines, Bayesian networks, etc. In each case, system 100 uses machine learning algorithms to generate probability information with respect to the B-mode input data that may then be used to estimate the volume of the target organ of interest, as described in detail below.

Figure 4:
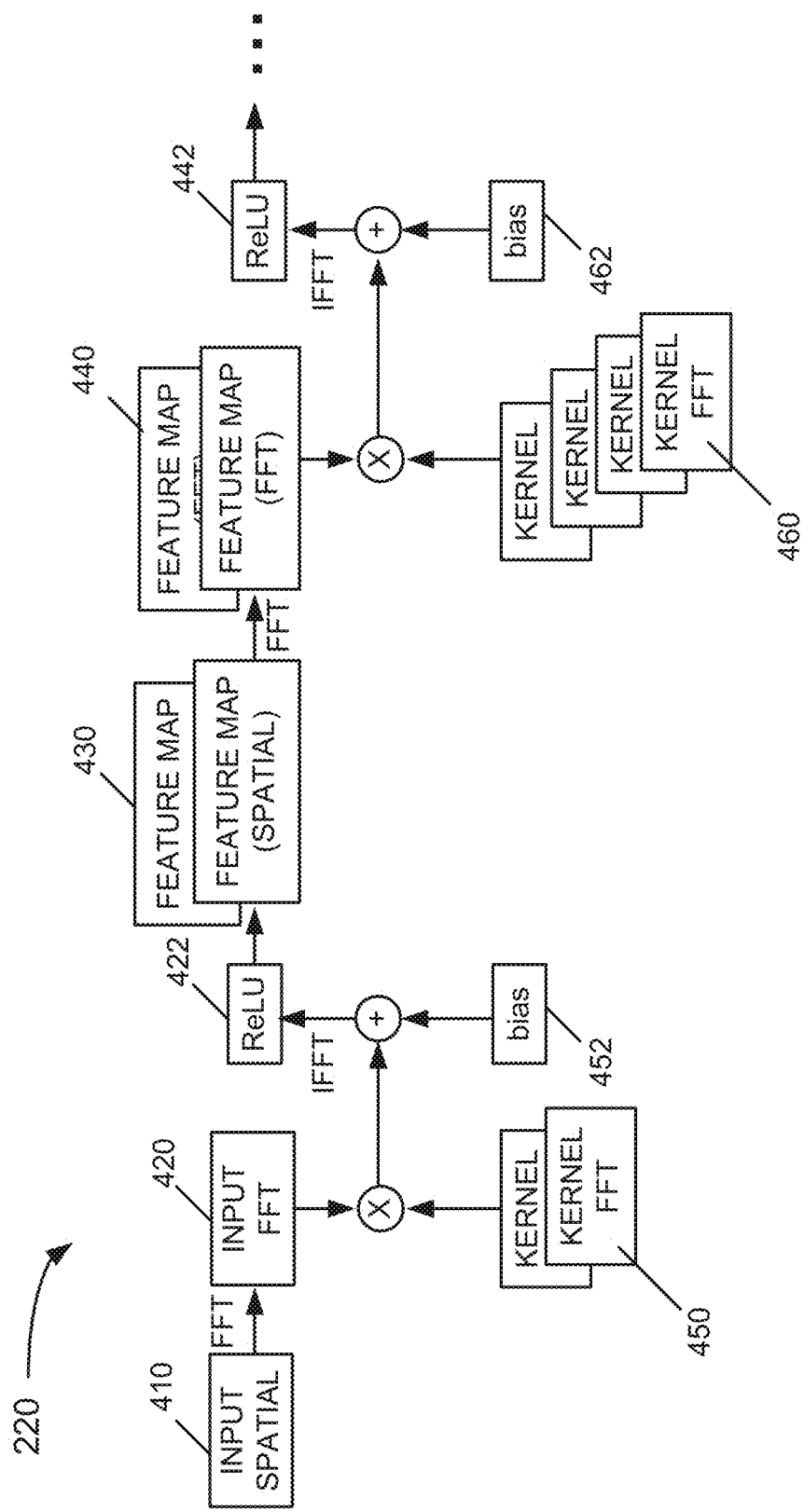
FIG. 4 illustrates a portion of autoencoder unit of FIG. 2 in an exemplary implementation.

FIG. 4 schematically illustrates a portion of CNN autoencoder unit 220 consistent with an exemplary implementation. Referring to FIG. 4, CNN autoencoder unit 220 may include spatial input 410, FFT input 420, lookup 422, feature maps 430, feature maps 440, lookup 442, kernels 450, bias 452, kernels 460 and bias 462. Input spatial 410 may represent 2D B-mode image data provided by data acquisition unit 210. CNN autoencoder 220 may perform a Fast Fourier Transform (FFT) to convert the image data into a frequency domain, apply filters or weights to the input FFT via kernels FFT 450. The output of the convolution processing may be biased via biasing value 452 and an inverse Fast Fourier Transform (IFFT) function applied with the result sent to look up table 422 to generate spatial feature maps 430. CNN autoencoder unit 220 may apply a FFT to spatial feature maps 430 to generate FFT feature maps 440 and the process may repeat for the additional convolutions and kernels. For example, if CNN autoencoder unit 220 includes eight convolutional layers, the process may continue seven more times. In addition, the kernels applied to each succeeding feature map correspond to the number of kernels times the number of feature maps, as illustrated by the four kernels 460 in FIG. 4. Biases 452 and 462 may also be applied to improve performance of the CNN processing.

As described above, CNN autoencoder unit 220 may perform convolutions in the frequency domain using FFTs. Such an approach allows system 100 to implement CNN algorithms using less computational power than larger systems that may use multiple computers to perform the CNN algorithms. In this manner, system 100 may use a hand-held unit and base station, such as probe 110 and base unit 120, to perform CNN processing. In other implementations, a spatial-domain approach may be used. A spatial-domain approach may use additional processing power in situations where system 100 is able to communicate with other processing devices, such as with processing devices connected to system 100 via a network (e.g., a wireless or wired network) and/or operating with system 100 via a client/server approach (e.g., system 100 is the client).

The output of CNN autoencoder unit 220 is probability information associated with a probability that each processed portion or pixel of the processed input image is within the target organ of interest. For example, CNN autoencoder unit 220 may generate a probability map in which each pixel associated with the processed input image data is mapped to a probability corresponding to a value between 0 and 1, where the value zero represents 0% probability that the pixel is within the target organ and the value one represents 100% probability that the pixel is within the target organ, as described in more detail below. CNN autoencoder unit 220 performs the pixel analysis or spatial location analysis on the processed images, as opposed to the input images. As a result, the pixel-by-pixel analysis of the processed images may not correspond on a one-to-one basis with the input images. For example, one processed pixel or spatial location analyzed by CNN autoencoder unit 220 to generate probability information may correspond to multiple pixels in the input image, or vice versa, based on resizing of the input images. In addition, the term "probability" as used herein should be construed to broadly include a likelihood that a pixel or portion of an image is within a target or organ of interest. The term "probability information" as used herein should also be broadly construed to include discrete values, such as binary values or other values.

In other implementations, CNN autoencoder unit 220 may generate a probability map in which each pixel is mapped to various values that can be correlated to probability values or indicators, such as values ranging from −10 to 10, values corresponding to one of 256 gray scale values, etc. In each case, the values or units generated by CNN autoencoder unit 220 may be used to determine the probability that a pixel or portion of an image is within the target organ. For example, in the 256 gray scale example, a value of one may indicate a 0% probability that a pixel or portion of an image is within the target organ and a value of 256 may indicate a 100% probability that a pixel or image is within the target organ.

In still other implementations, CNN autoencoder unit 220 may generate discrete output values, such as binary values, that indicate whether a pixel or output area is within the target organ. For example, CNN autoencoder unit 220 may include a binarization or classification process that generates a discrete value, such as a "1" when the pixel is within the target organ and a "0" when the pixel is not within the target organ. In other instances, the generated values may not be binary, but may correlate to whether the pixel is within the target organ or outside the target organ.

In some implementations, CNN autoencoder unit 220 may take various factors into consideration when analyzing the pixel-by-pixel data. For example, CNN autoencoder unit 220 may receive input from a user via the GUI displayed on display 122 of base unit 120 (FIG. 1A) indicating whether patient 150 is male, female or a child, and adjust the probability values based on stored information regarding likely sizes, shapes, volumes, etc., regarding the target organ for that particular type of patient. In such implementations, CNN autoencoder unit 220 may include thee three different CNNs trained with male, female and child data and CNN autoencoder unit 220 may use the appropriate CNN based on the selection.

In some implementations, CNN autoencoder unit 220 may automatically identify patient demographics of the subject, such as the gender, age, age range, adult or child status, etc., using, for example, the B-mode image data associated with the subject. CNN autoencoder unit 220 may also automatically identify clinical conditions of the subject using, for example, the B-mode image data, such as the body mass index (BMI), the body size and/or weight, etc. CNN autoencoder unit 220 may also automatically identify device information for a scan performed by system 100, such as position information of probe 110, aiming quality of probe 110 with respect to the target of interest, etc.

In other implementations, another processing device (e.g., similar to autoencoder unit 220 and/or processor 520) may perform the automatic detection of patient demographics, clinical conditions and/or device information using, for example, another neural network or other processing logic, and the output of the automatic determination may be provided as an input to CNN autoencoder unit 220. In addition, in other implementations, patient demographic information, clinical conditions and/or device information, patient data, etc., may be manually entered via, for example, display 122 of base unit 120 or via input selections on probe 110. In each case, the information automatically identified by CNN autoencoder unit 220 or manually input to CNN autoencoder unit 220/system 100 may be used to select an appropriate CNN for the processing of the image data.

In still other implementations, CNN autoencoder unit 220 may be trained with other information. For example, CNN autoencoder unit 220 may be trained with patient data associated with the subject, which may include information obtained using the patient's medical history data as well as information obtained via a physical examination of the patient prior to scanning a target of interest. For example, patient data may include a patient's medical history information, such as patient surgery history, chronic disease history (e.g., bladder disease information), previous images of the target of interest (e.g., previous images of the subject's bladder), etc., as well as data obtained via a physical examination of the patient/subject, such as pregnancy status, presence of scar tissue, hydration issues, abnormality in the target region (e.g., a bloated or distended abdomen), etc. In an exemplary implementation, the patient data may be input to system 100 via display 122 of base unit 120. In each case, the information automatically generated by CNN autoencoder unit 220 and/or another processing device, and/or information entered manually to system 100, may be provided as inputs to the machine learning processing performed by system 100 to aid in increasing the accuracy of data associated with the target of interest generated by system 100.

In still other instances, autoencoder unit 220 may receive input information regarding the type of organ (e.g., bladder, aorta, prostate, heart, kidney, uterus, a blood vessel, amniotic fluid, a fetus, etc.) via the GUI provided on display 122, the number of organs, etc., being imaged and use an appropriate CNN trained in accordance with the selected organ.

Post processing unit 230 includes logic to receive the pixel-by-pixel probability information and applies a "smart" binarization probability algorithm. For example, post processing unit 230 may perform interpolation to more clearly define contour details, as described in detail below. In addition, post processing unit 230 may adjust the output of CNN autoencoder unit 220 based on the subject type. For example, if a "child" is selected via the GUI on display 122 prior to initiating an ultrasound scan using probe 110, post processing unit 230 may ignore output from CNN autoencoder unit 220 that corresponds to a location that is deeper than a certain depth because the depth of the bladder within a child is typically shallow, due to the small size of a typical child. As another example, post processing unit 230 may determine based on the organ type, whether to select a single dominant region or multiple regions of interest. For example, if the organ type being scanned is the bladder, post processing unit 230 may select a single dominant region because there is only one bladder in the body. However, if the target is the pubic bone, post processing unit 230 may select up to two regions of interest, corresponding to the two sides of the pubic bone.

Aiming logic 240 includes logic to determine whether the target organ is properly centered with respect to probe 110 during the ultrasound scanning. In some implementations, aiming logic 240 may generate text or graphics to guide the user in adjusting the location of probe 110 to obtain a better scan of the target organ. For example, aiming logic 240 may analyze data from probe 110 and determine that probe 110 needs to be moved to the left on patient 150. In this case, aiming logic 240 may output text and/or graphics (e.g., flashing arrows) to display 122 to direct the user to move probe 110 in the appropriate direction.

Volume estimating logic 250 may include logic to estimate the volume of the target organ. For example, volume estimating logic 250 may estimate the volume based on the 2D images generated by post processing unit 230, as described in detail below. In scenarios where 3D images are provided, volume estimating logic 250 may simply determine the volume of the target organ using the 3D images. Volume estimating logic 250 may output the estimated volume via display 122 and/or a display on probe 110.

The exemplary configuration illustrated in FIG. 2 is provided for simplicity. It should be understood that system 100 may include more or fewer logic units/devices than illustrated in FIG. 2. For example, system 100 may include multiple data acquisition units 210 and multiple processing units that process the received data. In addition, system 100 may include additional elements, such as communication interfaces (e.g., radio frequency transceivers) that transmit and receive information via external networks to aid in analyzing ultrasound signals to identify a target organ of interest.

In addition, various functions are described below as being performed by particular components in system 100. In other implementations, various functions described as being performed by one device may be performed by another device or multiple other devices, and/or various functions described as being performed by multiple devices may be combined and performed by a single device. For example, in one implementation, CNN autoencoder unit 220 may convert input images into probability information, generate intermediate mapping outputs, as described below, and also convert the intermediate outputs into, for example, volume information, length information, area information, etc. That is, a single neural network processing device/unit may receive input image data and output processed image output data along with volume and/or size information. In this example, a separate post processing unit 230 and/or volume estimating logic 250 may not be needed. In addition, in this example, any intermediate mapping outputs may or may not be accessible or visible to an operator of system 100 (e.g., the intermediate mappings may be part of internal processing not directly accessible/visible to the user). That is, the neural network included in system 100 (e.g., CNN autoencoder unit 220) may convert received ultrasound echo information and/or images and output volume information or other size information for the target of interest, while requiring no additional input or little additional input by the user of system 100.

Figure 5:
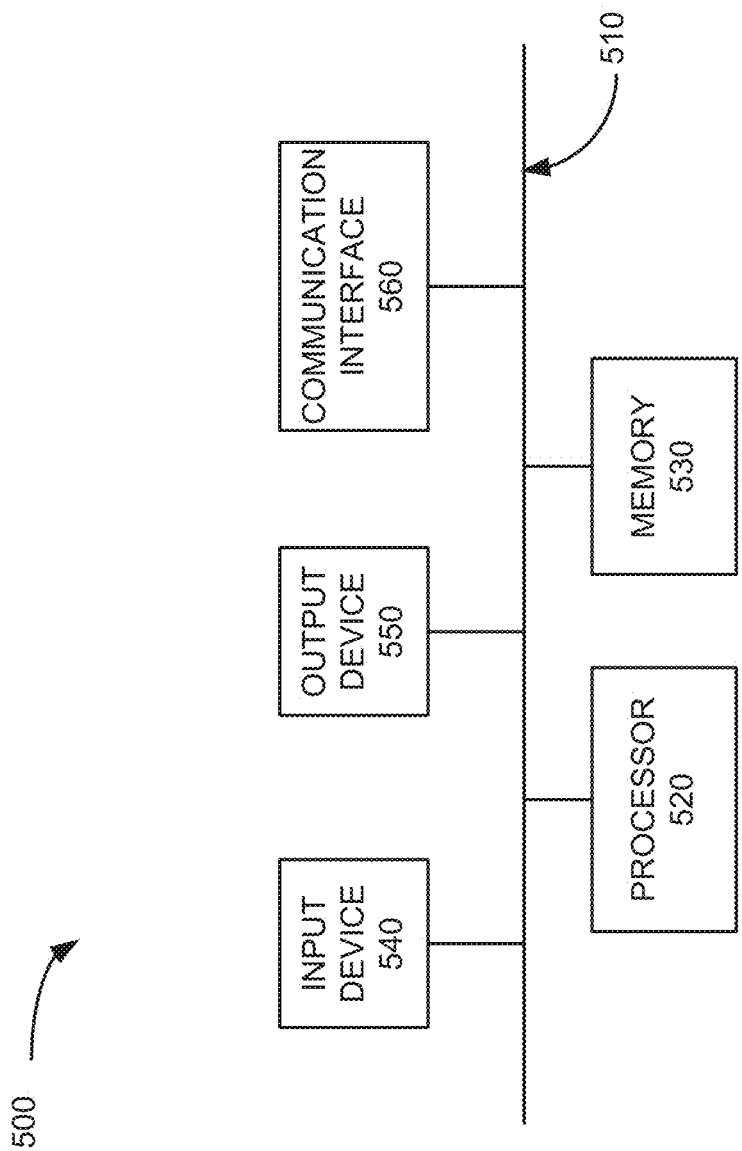
FIG. 5 illustrates an exemplary configuration of components included in one or more of the elements of FIG. 2.

FIG. 5 illustrates an exemplary configuration of a device 500. Device 500 may correspond to, for example, a component of CNN autoencoder unit 220, post processing unit 230, aiming logic 240 and volume estimating logic 250. Referring to FIG. 5, device 500 may include bus 510, processor 520, memory 530, input device 540, output device 550 and communication interface 560. Bus 510 may include a path that permits communication among the elements of device 500. In an exemplary implementation, all or some of the components illustrated in FIG. 5 may be implemented and/or controlled by processor 520 executing software instructions stored in memory 530.

Processor 520 may include one or more processors, microprocessors, or processing logic that may interpret and execute instructions. Memory 530 may include a random access memory (RAM) or another type of dynamic storage device that may store information and instructions for execution by processor 520. Memory 530 may also include a read only memory (ROM) device or another type of static storage device that may store static information and instructions for use by processor 520. Memory 530 may further include a solid state drive (SDD). Memory 530 may also include a magnetic and/or optical recording medium (e.g., a hard disk) and its corresponding drive.

Input device 540 may include a mechanism that permits a user to input information to device 500, such as a keyboard, a keypad, a mouse, a pen, a microphone, a touch screen, voice recognition and/or biometric mechanisms, etc. Output device 550 may include a mechanism that outputs information to the user, including a display (e.g., a liquid crystal display (LCD)), a printer, a speaker, etc. In some implementations, a touch screen display may act as both an input device and an output device.

Communication interface 560 may include one or more transceivers that device 500 uses to communicate with other devices via wired, wireless or optical mechanisms. For example, communication interface 560 may include one or more radio frequency (RF) transmitters, receivers and/or transceivers and one or more antennas for transmitting and receiving RF data via a network. Communication interface 560 may also include a modem or an Ethernet interface to a LAN or other mechanisms for communicating with elements in a network.

The exemplary configuration illustrated in FIG. 5 is provided for simplicity. It should be understood that device 500 may include more or fewer devices than illustrated in FIG. 5. In an exemplary implementation, device 500 performs operations in response to processor 520 executing sequences of instructions contained in a computer-readable medium, such as memory 530. A computer-readable medium may be defined as a physical or logical memory device. The software instructions may be read into memory 530 from another computer-readable medium (e.g., a hard disk drive (HDD), SSD, etc.), or from another device via communication interface 560. Alternatively, hard-wired circuitry, such as application specific integrated circuits (ASICs), field programmable gate arrays (FPGAs), etc., may be used in place of or in combination with software instructions to implement processes consistent with the implementations described herein. Thus, implementations described herein are not limited to any specific combination of hardware circuitry and software.

Figure 6:
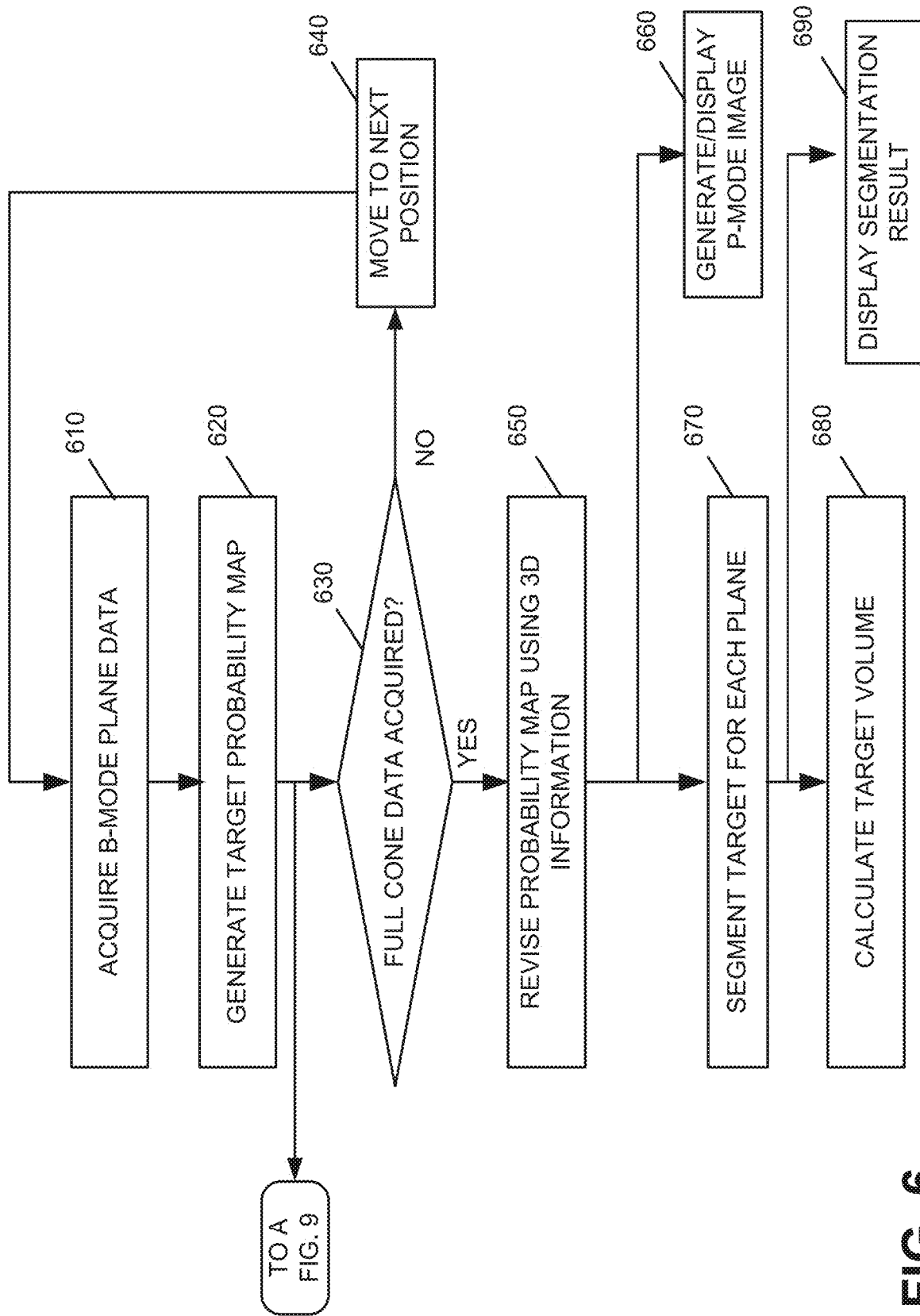
FIG. 6 is a flow diagram illustrating processing by various components illustrated in FIG. 2 in accordance with an exemplary implementation.

FIG. 6 is a flow diagram illustrating exemplary processing associated with identifying a target of interest, as well as identifying parameters (e.g., volume) associated with the target of interest. Processing may begin with a user operating probe 110 to scan a target organ of interest. In this example, assume that the target organ is a bladder. It should be understood that features described herein may be used to identify other organs or structures within the body.

In an exemplary implementation, a user may press trigger 114 and the transceiver included in probe 110 transmits ultrasound signals and acquires B-mode data associated with echo signals received by probe 110 (block 610). In one implementation, data acquisition unit 210 may transmit ultrasound signals on 12 different planes through the bladder and generate 12 B-mode images corresponding to the 12 different planes. In this implementation, the data may correspond to 2D image data. In other implementations, data acquisition unit 210 may generate 3D image data. For example, as discussed above with respect to FIG. 3, data acquisition unit 210 may perform interlaced scanning to generate 3D images. In each case, the number of transmitted ultrasound signals/scan planes may vary based on the particular implementation. As described above, in some implementations, data acquisition unit 210 may reduce the size of the B-mode images before forwarding the B-mode data to CNN autoencoder unit 220. For example, data acquisition unit 210 may reduce the size of the B-mode images by 10% or more.

In each case, assume that CNN autoencoder unit 220 receives 2D B-mode data and processes the data to remove noise from the received data. For example, referring to FIG. 7, CNN autoencoder unit 220 may receive B-mode image data 710, with a dark area or region 712 corresponding to the bladder. As illustrated, the B-mode image data includes areas that are irregular or may appear unclear or fuzzy to a user. For example, region 712 in FIG. 7 includes lighter areas within the perimeter of the bladder, as well as boundaries that are not distinct. Such noisy areas may make it difficult to accurately estimate the volume of the bladder.

In this case, CNN autoencoder unit 220 performs a de-noising of the acquired B-mode image 710 by generating a target probability map (block 620). For example, as discussed above, CNN autoencoder 220 may utilize CNN techniques to generate probability information with respect to each pixel in the input image.

Base unit 120 may then determine whether the full cone data (i.e., all of the scan plane data) has been acquired and processed (block 630). For example, base unit 120 may determine whether all 12 B-mode images corresponding to 12 different scans through the bladder have been processed. If all the B-mode image data has not been processed (block 630—no), base unit 120 controls motion to the next scan plane position (block 640) and processing continues to block 610 to process the B-mode image associated with another scan plane.

If all the B-mode image data has been processed (block 630—yes), base unit 120 may revise the probability map using 3D information (block 650). For example, CNN autoencoder unit 220 may use stored assumption information regarding the 3D shape and size of the bladder based on whether the patient is male, female, a child, etc., to modify some of the probability information generated by CNN autoencoder unit 220, thereby effectively modifying the size and/or shape of the bladder. That is, CNN autoencoder unit 220, as described above, may use a CNN trained based on demographic information of the patient, clinical conditions of the patient, device information associated with system 100 (e.g., probe 110), patient data (e.g., patient medical history information and patient examination data) of the patient, etc. For example, CNN autoencoder unit 220 may use a CNN trained with male patient data if patient 150 is male, use a CNN trained with female patient data if patient 150 is female, use a CNN trained with child data if patient 150 is a child, use a CNN trained based on the patient's age range, use a CNN trained with the patient's medical history, etc. In other implementations, such as when 3D image data is received and processed by base unit 120, no additional processing may be performed and block 650 may be skipped. In either case, system 100 may display the P-mode image data (block 660), such as image 720 illustrated in FIG. 7.

In either case, base unit 120 may use the probability map to segment the target region via a binarization process (block 670). For example, post-processing unit 230 may receive the output of CNN autoencoder unit 220 and resize (e.g., via interpolation), smooth and/or de-noise (e.g., via filtering) the probability mapping. For example, in one implementation, the probability map may be resized through interpolation to a larger size to obtain better resolution and/or to recover, at least partially, the spatial resolution of the original B-mode image data that may have been reduced in size. In one implementation, a 2D Lanczos interpolation may be performed to resize the image associated with the target probability map.

In addition, base unit 120 may perform a classification or binarization process to convert the probability information from probability mapping unit to binarized output data. For example, post processing unit 230 may convert the probability values to binary values. When multiple candidate probability values are identified for a particular pixel, post processing unit 230 may select the most prominent value. In this manner, post processing unit 230 may apply some "smartness" to select the most likely value when multiple candidates are identified.

Figure 8:
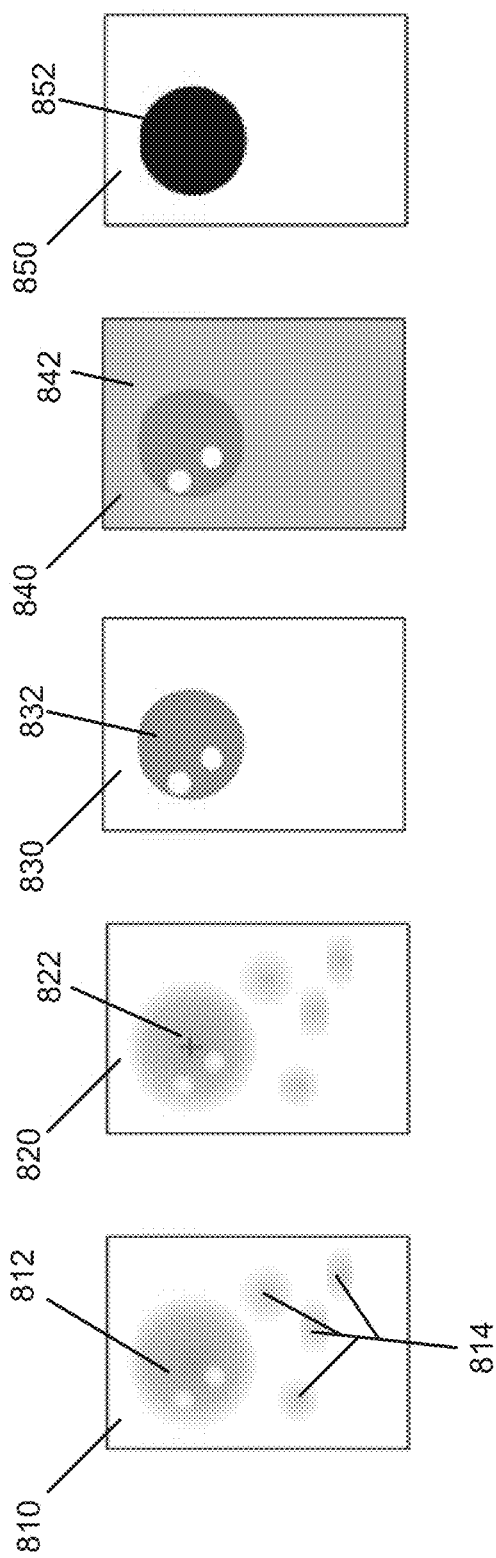
FIG. 8 illustrates a binarization process in accordance with the processing of FIG. 6.

FIG. 8 schematically illustrates an exemplary smart binarization process. Referring to FIG. 8, image 810 illustrates an output from a pixel classification or probability map corresponding to a 2D ultrasound image in which the probability information is converted to gray scale images having various intensities. As illustrated, image 810 includes a gray area labeled 812 and gray areas labeled 814 that represent possible locations for portions of the bladder. Post processing unit 230 identifies the peak point or point within image 810 having the greatest intensity, as illustrated by cross-hairs 822 illustrated in image 820. Post-processing unit 230 may then fill the region around the peak point for regions whose intensity are greater than a threshold intensity, as illustrated by region 832 in image 830. In this case, regions within area 820 whose threshold intensity value is less than the threshold intensity do not get filled, resulting in the removal of gray areas 814 shown in image 810. Post-processing unit 230 may then fill the background, as illustrated by region 842 in image 840. Post processing unit 230 then fills any holes or open regions within the image, as illustrated in area 852 in image 850. The holes in region 842 may correspond to noisy regions or regions associated with some obstruction in patient 150. In this manner, post processing unit 230 identifies the most probable location and size for the bladder. That is, area 852 is considered to be part of the bladder of patient 150.

In other implementations, post processing unit 230 may use information other than a peak intensity value within image 810. For example, post processing unit 230 may use a peak value of a processed probability, such as a peak of a smoothed probability map, use multiple peak values to identify multiple filled regions, etc. As other examples, post processing unit 230 may select a "dominant" region based on area, peak probability or averaged probability in each region. In still other implementations, post processing unit 230 may use one or multiple seed points manually input by an operator via, for example, display 122, use an algorithm that generates one or more seed points, perform another type of thresholding that does not use seed points, etc., to identify regions of the patient's bladder.

Figure 7:
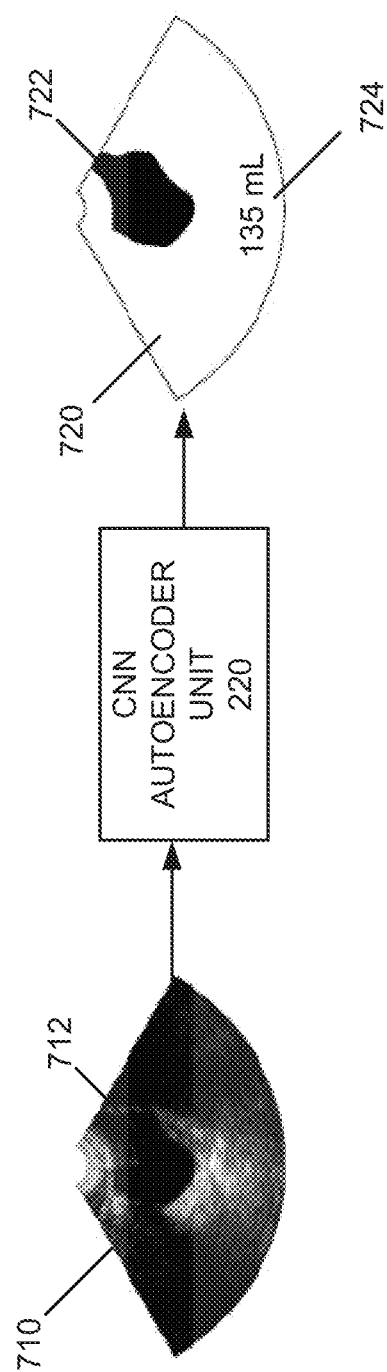
FIG. 7 illustrates output generated by the autoencoder of FIG. 2 in an exemplary implementation.

After image 810 is processed in this manner, base unit 120 may output an image, such as image 720 illustrated in FIG. 7. Referring to FIG. 7, image 720 includes region 722 corresponding to the bladder. As illustrated, the edges of bladder 722 are much more distinct than the boundaries in image 712, providing a much more accurate representation of the bladder. In this manner, base unit 120 may use brightness values for each pixel and local gradient values for adjacent pixels, as well as statistical methods, such as a hidden Markov model and neural network algorithms (e.g., CNN) to generate the probability value for each pixel in the B-mode image and de-noise the B-mode data.

Base unit 120 may then convert the segmentation results to a target volume (block 680). For example, post processing unit 230 may sum the volumes of all voxels in 3D space that correspond to each valid target pixel in the binarized maps. That is, volume estimating logic 250 may sum the voxels in the 12 segmented target images to estimate the volume of the bladder.

For example, the contribution or volume of each voxel can be pre-calculated and stored in a lookup table within base unit 120. In this case, volume estimating logic 250 may use the sum of the voxels as an index to the lookup table to determine the estimated volume. Volume estimating logic 250 may also display the volume via display 122 of base unit 120. For example, volume estimating logic 250 may display the estimated volume of the bladder at area 724 in FIG. 7 (i.e., 135 milliliters (mL) in this example), which is output to display 122 of base unit 120. Alternatively, volume estimating logic 250 may display the volume information via a display on probe 110. Post processing unit 230 may also display the segmentation results (block 690). That is, post processing unit 230 may display 12 segments of the bladder via display 122 of base unit 120.

In some implementations, system 100 may not perform a binarization process on the probability mapping information. For example, in some implementations, CNN auto encoder unit 220 and/or post processing unit 230 may apply a look-up table to the probability mapping information to identify likely portion of the target organ of interest and display the output via display 122.

Figure 9:
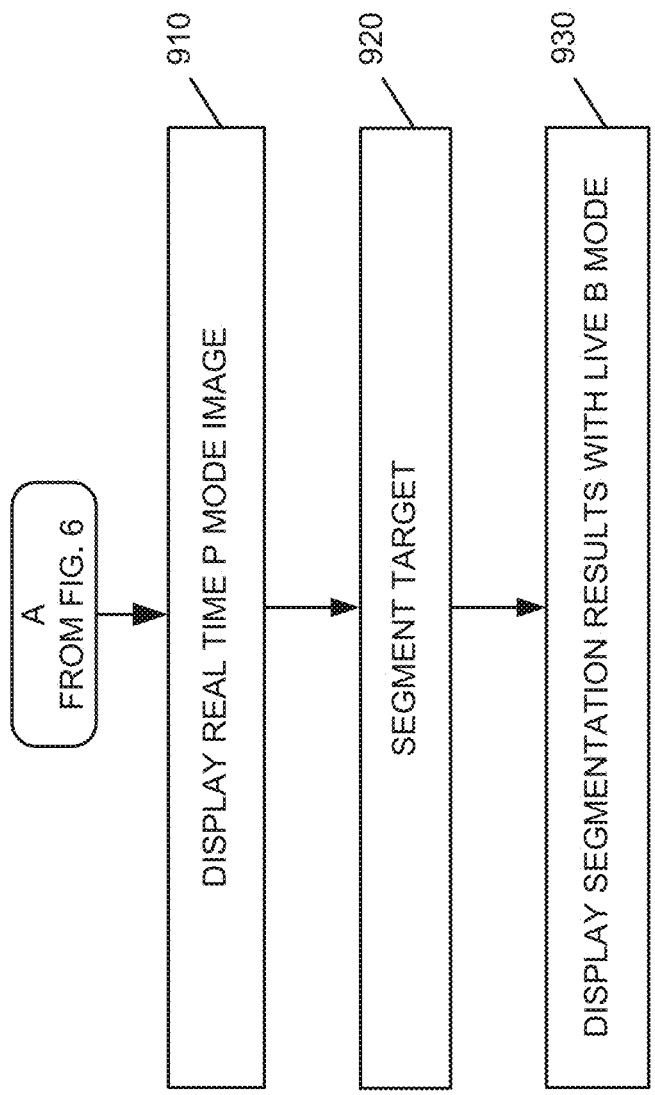
FIG. 9 is a flow diagram associated with displaying information via the base unit of FIG. 1A.
Figure 10:
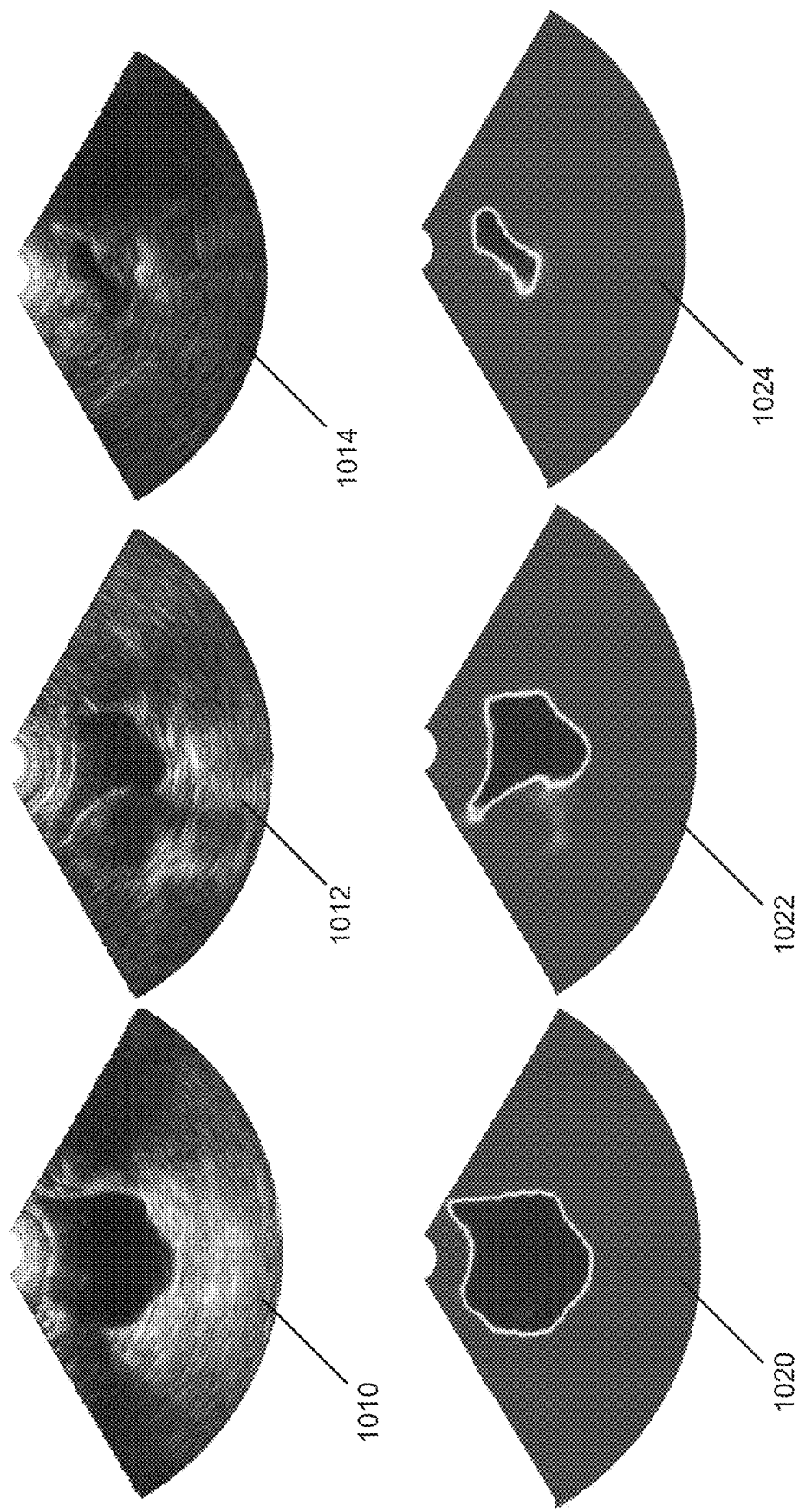
FIG. 10 illustrates exemplary image data output by the base unit in accordance with the processing of FIG. 9.

Referring back to block 620, in some implementations, probability mapping unit 230 may display information as it is generated in real time. FIG. 9 illustrates exemplary processing associated with providing additional display information to a user. For example, post processing unit 230 may display probability mode information (referred to herein as P-mode) via display 122 as it is generated in real time (FIG. 9, block 910). Post processing unit 230 may also segment the target (block 920) and display the segmentation results with the B-mode images (block 930). For example, FIG. 10 illustrates three B-mode images 1010, 1012 and 1014 and corresponding P-mode images 1020, 1022 and 1024. In other implementations, all 12 B-mode images and 12 corresponding P-mode images may be displayed. As illustrated, the P-mode images 1020, 1022 and 1024 are much clearer than the B-mode images 1010, 1012 and 1014. In addition, in some implementations, post processing unit 230 may provide outlines for the boundaries of the bladder displayed in each of the P-mode images. For example, each of P-mode images 1020, 1022 and 1024 may include outlines in, for example, a different color or brighter color than the interior portions of the bladder, as illustrated in FIG. 10.

Implementations described herein use machine learning to identify an organ or structure of interest in a patient based on information obtain via an ultrasound scanner. The machine learning processing may receive image data and generate probability information for each particular portion of the image (e.g., pixel) to determine the probability that the particular portion is within the target organ. Post processing analysis may further refine the probability information using additional information, such as the gender or age of the patient, the particular target organ, etc. In some instances, the volume of the target organ may also be provided to the user, along with real time probability mode images.

The foregoing description of exemplary implementations provides illustration and description, but is not intended to be exhaustive or to limit the embodiments to the precise form disclosed. Modifications and variations are possible in light of the above teachings or may be acquired from practice of the embodiments.

For example, features have been described above with respect to identifying a target of interest, such as a patient's bladder, and using CNN processing to estimate a volume of the target (e.g., bladder). In other implementations, other organs or structures may be identified, and sizes or other parameters associated with the organs/structures may be estimated. For example, the processing described herein may be used to identify and display a prostate gland, a kidney, a uterus, ovaries, an aorta, a heart, a blood vessel, amniotic fluid, a fetus etc., as well as particular features associated with these targets, such as volume and/or size-related measurements.

For example, in implementations in which the processing described herein is used in connection with various organs or targets other than the bladder (e.g., aorta, prostate, kidney, heart, uterus, ovaries, a blood vessel, amniotic fluid, a fetus, etc.), additional size-related measurements may be generated. For example, length, height, width, depth, diameter, area, etc., of an organ or region of interest may be calculated. As an example, for a scan of an aorta, measuring the diameter of the aorta may be important in trying to identify an anomaly, such as an aneurysm. For a prostate scan, measurement of the width and height of the prostate may be needed. In these cases, measurements such as length, height, width, depth, diameter, area, etc., may be generated/estimated using the machine learning processing described above. That is, the machine learning described above may be used to identify boundary walls or other items of interest and estimate the particular size-related parameter of interest to medical personnel.

In addition, features have been described above mainly with respect to generating B-mode images using echo data and applying machine learning to the B-mode images to identify volume, length or other information associated with the target. In other implementations, other types of ultrasound input image data may be used. For example, C-mode image data which typically includes a representation of the target of interest (e.g., bladder) formed in a plane oriented perpendicular to B-mode images may be used in other implementations. Still further, in other implementations, radio frequency (RF) or quadrature signals (e.g., IQ signals) may be used as input to CNN autoencoder unit 220 to generate a probability output mapping associated with the target.

Further, features have been described above with respect to generating a single probability map. In other implementations, multiple probability maps may be generated. For example, system 100 may generate one probability map for the target organ of interest (e.g., the bladder), another probability map for the pubic bone/pubic bone shadow, and another probability map for the prostate. In this manner, more accurate representations of the internal organs of patient 150 may be generated, which may result in more accurate volume estimation for the target organ (e.g., the bladder).

In addition, features described herein relate to performing a pixel-by-pixel analysis of B-mode image data. In other implementations, instead of a pixel-by-pixel mapping an edge map may be used. In this implementation, the edges of the target may be detected using CNN algorithms. In a further implementation, a polygon coordinate approach may be used to identify discrete portions of the bladder and then connect the points. In this implementation, a contour edge tracking algorithm may be used to connect the points of the target organ.

Still further, various inputs, such as information indicating whether the patient is male or female, a child, etc., have been described above. Other inputs to the probability mapping and/or binarization may also be used. For example, a body mass index (BMI), age or age range may be input to base unit 120 and base unit 120 may automatically adjust the processing based on the particular BMI, age or age range. Still other inputs to the probability mapping and/or binarization process, such as the depth of each pixel, plane orientation, etc., may be used to improve accuracy of the output images and/or volume estimate generated by system 100.

In addition, as described above, training data associated with various types of patients, men, women and children may be used to aid in generating the P-mode data. For example, thousands or more of training data images may be used to generate the CNN algorithms used to process the B-mode input data to identify the target or interest. In addition, thousands or more images may be input or stored in base unit 120 to aid in modifying the output of CNN autoencoder unit 220. This may be particularly helpful in scenarios where expected obstructions, such as a pubic bone for a bladder scan, adversely affect the images. In these implementations, base unit 120 may store information regarding how to account for and minimize effects of the obstruction. CNN autoencoder unit 220 and/or post processing unit 230 may then more accurately account for the obstruction.

Still further, features described herein refer to using B-mode image data as an input to CNN autoencoder unit 220. In other implementations, other data may be used. For example, echo data associated with transmitted ultrasound signals may include harmonic information that can be used to detect a target organ, such as the bladder. In this case, higher order harmonic echo information (e.g., second harmonic or higher) with respect to the frequency of the transmitted ultrasound signals may be used to generate probability mapping information, without generating B-mode images. In still other implementations, the higher order harmonic information may be used in addition to the B-mode data described above to enhance the P-mode image data. In still further implementations, probe 110 may transmit ultrasound signals at multiple frequencies and echo information associated with the multiple frequencies may be used as input to CNN autoencoder unit 220 or other machine learning modules to detect a target organ and estimate volume, size, etc., of the target organ.

For example, multiple B-mode images at the fundamental frequency and multiple B-mode images at the higher order harmonic frequency or frequencies may be used as inputs to CNN autoencoder unit 220. Still further, fundamental frequency and harmonic frequency information may be preprocessed and used as inputs to CNN autoencoder unit 220 to aid in generating the probability map. For example, the ratio between harmonics and fundamental frequency powers may be used as an input to the CNN autoencoder unit 220 to enhance the accuracy of the probability mapping.

In addition, in some implementations, the post processing described above may use a second machine learning (e.g., CNN) algorithm to de-noise the image data and/or perform outline/edge tracking for the images.

Still further, implementations have been described above with respect to data acquisition unit 210 obtaining 2-dimensional (2D) B-mode image data. In other implementations, higher dimensional image date (e.g., 2.5D or 3D) data may be input to CNN autoencoder unit 220. For example, for a 2.5D implementation, CNN autoencoder unit 220 may use B-mode images associated with several scan planes, as well as neighboring scan planes to improve accuracy. For a 3D implementation, CNN autoencoder unit 220 may generate 12 probability maps for each of 12 scan planes and post processing unit 230 may use all 12 probability maps to generate 3D images based on the 12 probability maps (e.g., via a 3D flood-filling algorithm). A classification and/or binarization process may then be performed on the 2.5D or 3D images to generate, for example, 3D output images.

Further, while series of acts have been described with respect to FIGS. 6 and 9, the order of the acts may be different in other implementations. Moreover, non-dependent acts may be implemented in parallel.

It will be apparent that various features described above may be implemented in many different forms of software, firmware, and hardware in the implementations illustrated in the figures. The actual software code or specialized control hardware used to implement the various features is not limiting. Thus, the operation and behavior of the features were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as one or more processors, microprocessor, application specific integrated circuits, field programmable gate arrays or other processing logic, software, or a combination of hardware and software.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A system, comprising:
   a hand-held probe configured to be positioned on an external surface of a patient's body, and configured to:
   transmit ultrasound signals to a target of interest, wherein the target of interest comprises the patient's bladder or prostate, and
   receive echo information associated with the transmitted ultrasound signals; and at least one processing device configured to:
   process the received echo information using a machine learning algorithm to generate probability information associated with the target of interest, wherein the probability information comprises a value indicating whether a portion of an image associated with the processed echo information is within the target of interest,
   process the probability information generated by the machine learning algorithm to identify the target of interest, wherein when processing the probability information, the at least one processing device is configured to binarize the probability information to identify portions of the image within the target of interest,
   calculate, based on the processed binarized probability information, a second value corresponding to a volume or size-related measurement associated with the target of interest,
   output image information corresponding to the target of interest based on the processed binarized probability information, and
   output the second value.

2. The system of claim 1, wherein when calculating the second value, the at least one processing device is further configured to:
   calculate, based on the binarized probability information, the second value, wherein the size-related measurement corresponds to at least one of a length, height, width, depth, diameter or area associated with the target of interest.

3. The system of claim 1, wherein when processing the received echo information, the at least one processing devices is configured to use a convolutional neural network algorithm.

4. The system of claim 1, further comprising:
   a display configured to receive the image information, display the image information and display the second value, wherein the second value corresponds to a volume of the bladder or the prostate.

5. The system of claim 4, wherein the display is further configured to:
   simultaneously display B-mode image data corresponding to the received echo information and the image information corresponding to the target of interest.

6. The system of claim 1, wherein the at least one processing device is further configured to:
   generate aiming instructions for directing the probe to the target of interest.

7. The system of claim 1, wherein the target of interest comprises the bladder.

8. The system of claim 1, wherein the at least one processing device is further configured to:
   receive information comprising at least one of gender information for a subject, information indicating that the subject is a child, age information, age range information, or body mass index information, and
   process the received echo information based on the received information.

9. The system of claim 1, wherein the at least one processing device is further configured to:
   automatically determine at least one of demographic information of a subject, clinical information of the subject, or device information associated with the probe, and
   process the received echo information based on the automatically determined information.

10. The system of claim 1, wherein when processing the received echo information, the at least one processing device is configured to:
    process the received echo information to generate output image data,
    process pixels associated with the output image data,
    determine values for each processed pixel,
    identify a peak value, and
    fill in an area around a point associated with the peak value to identify a portion of the target of interest.

11. The system of claim 1, wherein when processing the received echo information, the at least one processing device is configured to:
  identify higher order harmonic information with respect to a frequency associated with the transmitted ultrasound signals, and
  generate the probability information based on the identified higher order harmonic information.

12. The system of claim 1, wherein the probe is configured to transmit the received echo information to the at least one processing device via a wireless interface.

13. The system of claim 1, wherein the target of interest comprises the prostate.

14. The system of claim 1, wherein the at least one processing device is further configured to:
  receive information comprising at least one of medical history information of a subject or information obtained via a physical examination of the subject, and
  process the received echo information based on the received information.

15. The system of claim 1, wherein the at least one processing device is further configured to:
  output visual information associated with boundaries of the target of interest based on the processed binarized probability information.

16. A method, comprising: transmitting, via a hand-held ultrasound probe configured to be positioned on an external surface of a patient's body, ultrasound signals to a target of interest, wherein the target of interest comprises a bladder, a prostate gland or a kidney;
  receiving, via the hand-held ultrasound probe, echo information associated with the transmitted ultrasound signals;
  processing the received echo information using a machine learning algorithm to generate probability information associated with the target of interest, wherein the probability information comprises a value indicating whether a portion of an image associated with the processed echo information is within the target of interest;
  processing the probability information generated by the machine learning algorithm to identify the target of interest, wherein the processing the probability information comprises binarizing the probability information to identify portions of the image within the target of interest;
  calculating, based on the processed binarized probability information, a second value corresponding to a volume or size-related measurement associated with the target of interest;
  outputting image information corresponding to the target of interest based on the processed binarized probability information; and
  outputting the second value.

17. The method of claim 16, wherein calculating the second value comprises:
  calculating, based on the binarized probability information, the second value, wherein the size-related measurement corresponds to at least one of a length, height, width, depth, diameter or area associated with the target of interest; and
  outputting the second value to a display.

18. The method of claim 16, further comprising:
  simultaneously displaying B-mode image data corresponding to the echo information and the output image information corresponding to the target of interest.

19. The method of claim 16, further comprising:
  receiving, prior to transmitting the ultrasound signals to the target of interest, information comprising at least one of gender information for a subject, age information for the subject, age range information for the subject, body mass index information for the subject, body size of the subject, or weight of the subject; and
  processing the received echo information based on the received information.

20. A system, comprising:
  a memory; and
  at least one processing device configured to:
    receive, from a hand-held probe configured to be positioned on an external surface of a patient's body, image information corresponding to a target of interest, wherein the target of interest comprises a bladder, a prostate gland, a uterus, or a kidney,
    process the received image information using a machine learning algorithm to generate probability information associated with the target of interest,
    process the probability information generated by the machine learning algorithm to identify the target of interest, wherein when processing the probability information, the at least one processing device is configured to binarize the probability information to identify portions of the processed image information within the target of interest,
    calculate a value corresponding to a volume or size-related measurement associated with the target of interest,
    output second image information corresponding to the target of interest based on the processed binarized probability information, and
    output the value.

21. The system of claim 20, further comprising:
  a display,
wherein when calculating the value, the at least one processing device is further configured to:
  calculate, based on the processed binarized probability information, the value, wherein the size-related measurement corresponds to at least one of a length, height, width, depth, diameter or area associated with the target of interest; and
  output the value to the display.

22. The system of claim 20, wherein the machine learning algorithm comprises a convolutional neural network algorithm and the memory stores instructions to execute the convolutional neural network algorithm.

23. The system of claim 20, further comprising:
  the hand-held probe, wherein the hand-held probe is configured to:
    transmit ultrasound signals to the target of interest,
    receive echo information associated with the transmitted ultrasound signals, and
    forward the echo information to the at least one processing device,
  wherein the at least one processing device is further configured to:
    generate, using the machine learning algorithm, the image information corresponding to the target of interest based on the echo information.

* * * * *